(12) United States Patent
Nour

(10) Patent No.: US 8,333,731 B2
(45) Date of Patent: Dec. 18, 2012

(54) MEDICAL PULSATING DEVICE

(76) Inventor: Sayed Nour, Paris (FR)

(*) Notice: Subject to any disclaimer, the term of this patent is extended or adjusted under 35 U.S.C. 154(b) by 0 days.

(21) Appl. No.: 12/935,345

(22) PCT Filed: Apr. 2, 2009

(86) PCT No.: PCT/FR2009/050564
§ 371 (c)(1),
(2), (4) Date: Sep. 29, 2010

(87) PCT Pub. No.: WO2009/136034
PCT Pub. Date: Nov. 12, 2009

(65) Prior Publication Data
US 2011/0021987 A1    Jan. 27, 2011

(30) Foreign Application Priority Data
Apr. 2, 2008  (FR) ...................... 08 01816

(51) Int. Cl.
*A61M 25/00*    (2006.01)
(52) U.S. Cl. .................................... 604/99.01
(58) Field of Classification Search ............. 604/96.01, 604/97.01, 98.01, 99.01
See application file for complete search history.

(56) References Cited

U.S. PATENT DOCUMENTS

| | | | |
|---|---|---|---|
| 4,362,150 A | 12/1982 | Lombardi, Jr. et al. | |
| 4,902,273 A | 2/1990 | Choy et al. | |
| 5,090,957 A | 2/1992 | Moutafis et al. | |
| 5,697,906 A | 12/1997 | Ariola et al. | |
| 5,718,861 A * | 2/1998 | Andrews et al. | 264/235 |
| 5,759,175 A | 6/1998 | Ariola et al. | |
| 5,817,001 A * | 10/1998 | Leschinsky et al. | 600/18 |
| 5,910,103 A * | 6/1999 | Saper et al. | 600/18 |
| 6,149,578 A * | 11/2000 | Downey et al. | 600/18 |
| 6,190,304 B1 * | 2/2001 | Downey et al. | 600/18 |
| 6,346,092 B1 | 2/2002 | Leschinsky | |
| 6,666,814 B2 * | 12/2003 | Downey et al. | 600/18 |
| 6,733,459 B1 | 5/2004 | Atsumi | |
| 7,250,025 B2 * | 7/2007 | Nigroni et al. | 600/17 |

FOREIGN PATENT DOCUMENTS
WO     2008000110     1/2008

* cited by examiner

*Primary Examiner* — Nicholas Lucchesi
*Assistant Examiner* — Aarti B Berdichevsky
(74) *Attorney, Agent, or Firm* — Trego, Hines & Ladenheim, PLLC

(57) ABSTRACT

The invention relates to a novel pulsating medical device comprising: a catheter (1) designed to be inserted into a blood vessel, having a diameter and comprising a rod at its insertion end, termed part A; and an inflatable component (6) housed around part of the catheter (1), termed part B, said inflatable component (6) being designed to be connected to an inflation means (9) connected to the other end of said catheter (1) and termed part C, so that said inflatable component can be inflated/deflated in a pulsed manner, the diameter of part B of said catheter (1) being less than the diameters of parts A and C of said catheter (1), and the diameters of parts A and C of said catheter (1) being approximately equal.

14 Claims, 2 Drawing Sheets

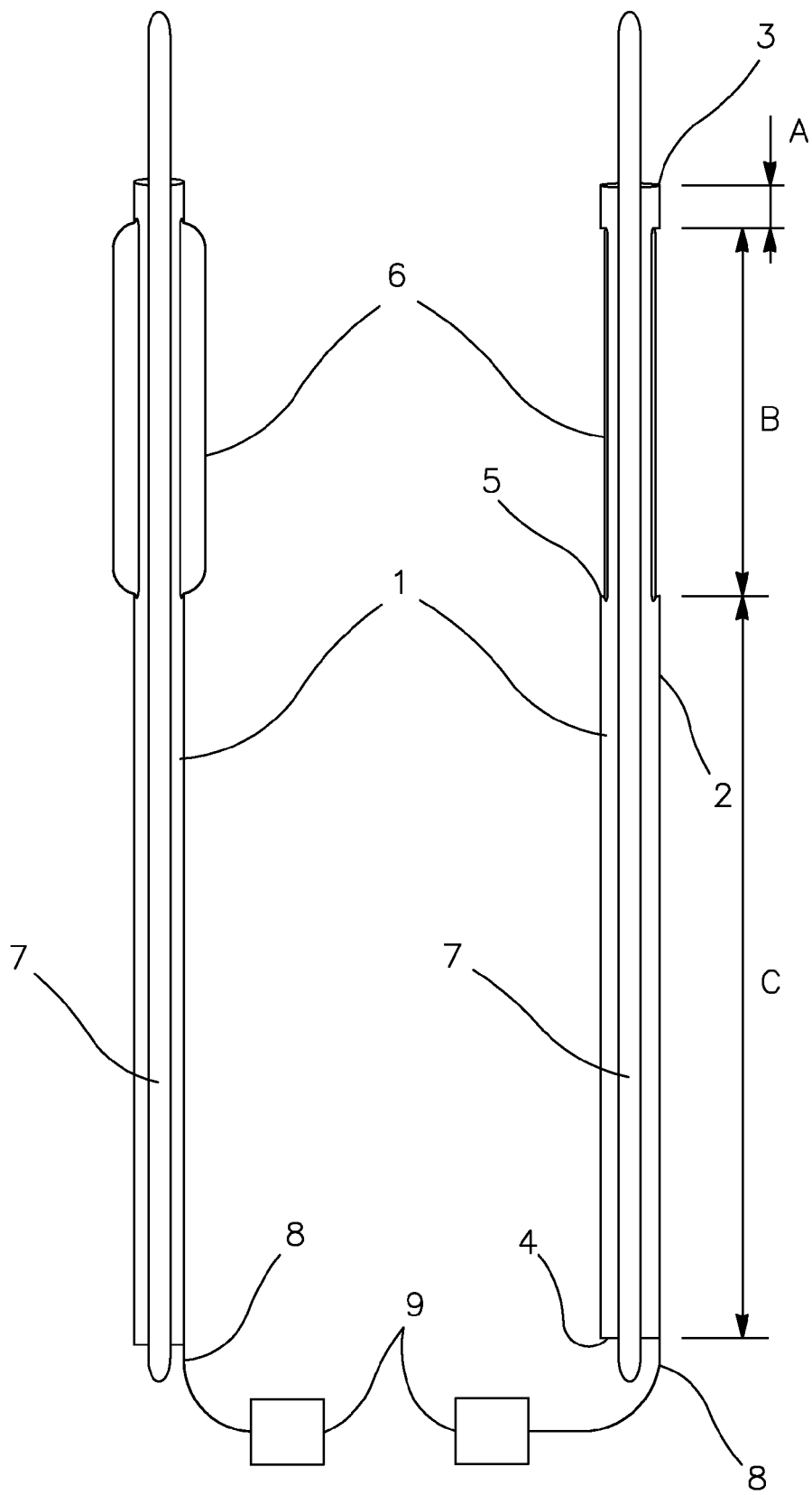

MEDICAL PULSATING DEVICE

The present invention relates to a novel pulsating medical device.

Conceptually, the cardiovascular system is a pressurised closed hydraulic circuit, lined internally with epithelial cells. The function of these epithelial cells is regulated by cardiac pulsation inducing pressure variations in vessels and thus shearing of these cells, stimulating same. These tangential shear stress forces are essential for maintaining the endothelial function including vascular tonicity by means of nitric oxide synthesis (NOS), blood clotting, the inflammatory response, immunity, atherosclerosis, angiogenesis and apoptosis. The endothelial function is very important since it controls embryogenesis, morphogenesis, organogenesis and health body maintenance.

Any intervention on this circuit, such as, for example, a disease or a surgical operation, induces endothelial dysfunction with potentially dramatic consequences.

In the field of circulatory assistance, numerous pulsating devices are currently used. Of these pulsating devices, the most used due to the easy use thereof and the inexpensiveness thereof is the intra-aortic balloon pump (IABP).

Patent application US 2001/0031907 discloses a pulsating blood circulation assistance device comprising:
- a catheter, to be inserted into a blood vessel, having a diameter and comprising a rod at the insertion end thereof and,
- an inflatable component housed around part of the catheter, increasing, when inflated, the diastolic pressure in the coronary arteries, said inflatable component being designed to be connected to an inflation means, positioned at the other end of said catheter, so that said inflatable component can be inflated/deflated in a pulsed manner.

At the present time, when it is required to insert an inflatable component catheter or balloon of the abovementioned type into a patient's blood vessel, an insertion device, consisting of a guide type and an anti-reflux haemostatic valve is used. The insertion of the guide tube creates an opening having a sufficient diameter to subsequently insert the balloon catheter inside said guide tube whereas the valve, positioned at the insertion point, makes it possible to reduce and stop the blood flow via the insertion device.

The drawback involved with the balloon catheters according to the prior art is that, if it is required to insert said balloon catheter not through an insertion device but directly into the blood vessel, as is the case, for example, when it is required to leave a balloon catheter in position for a certain time or for small-diameter catheters (i.e. in the region of a few millimeters or less), the blood flow risks are not negligible. Indeed, during the direct insertion of the balloon catheter, the diameter of the insertion point, which is initially equal to the diameter of the catheter, is enlarged following the passage of the portion of the catheter surrounded by the balloon. Subsequently, when the catheter is inserted more deeply so as to position the balloon in the region to be treated, the diameter of the catheter is less than the diameter of the insertion point, hence blood flow risks.

Therefore, the invention addresses this problem by means of a pulsating medical device comprising:
- a catheter, to be inserted into a blood vessel, having a diameter and comprising a rod at the insertion end thereof, referred to as part A, and,
- an inflatable component housed around part of the catheter, referred to as part B, said inflatable component being designed to be connected to an inflation means positioned at the other end of said catheter, referred to as part C, so that said inflatable component can be inflated/deflated in a pulsed manner characterised in that the diameter of part B of the catheter is less than the diameters of parts A and C of the catheter and in that the diameters of parts A and C of said catheter are substantially equal.

This reduction in the diameter of part B of the catheter enables the diameter of the whole of part B of the catheter plus the inflatable component to be reduced with respect to that of catheters according to the prior art. Following the insertion of the catheter into a patient's blood vessel, excessive widening of said insertion point due to a markedly greater diameter of part of the catheter will not occur.

In one particular embodiment of the invention, the diameter of part B of the catheter plus the deflated inflatable component is less than or equal to the diameters of parts A and C of the catheter. In this embodiment, the insertion of the catheter does not cause any widening of the insertion point, which is more advantageous.

In one particular embodiment, the inflatable component is a balloon.

Preferably, the inflatable component is formed from a biocompatible radio-opaque material. The insertion of said inflatable component into a blood vessel thus does not cause any infection or other damage and can be viewed readily by means of radiography.

In one particular embodiment, said material is polyurethane; this material is one example, among others, of advantageous organic material.

In one particular embodiment of the invention, the diameter of the catheter is a few millimeters or less. These dimensions correspond to small catheters used in paediatrics and also in adults to reach some small blood vessels. However, the problem addressed by the invention, that of varying the diameter of a balloon catheter when the use thereof without a guide tube is required, is increased significantly in the case of small-diameter catheters. Indeed, for these small catheters, the thickness of the balloon represents a proportionally markedly greater increase in the diameter thereof, in relation to larger diameter catheters.

In one particular embodiment of the invention, the dimensions of the inflatable component are a length between 0.1 and 2 cm and a volume between 0.1 and 2 $cm^3$.

The invention also relates to a pulsating medical assembly comprising a pulsating device, as described above, and inflation means comprising:
- a bag, suitable for being filled with fluid,
- bag compression means, suitable for compressing said bag in a pulsed manner; and
- connection means connecting said bag to said inflatable component of the catheter, enabling the circulation of the fluid between said inflatable component and said bag.

This pulsating medical assembly is simple to use and inexpensive. Furthermore, due to the compact size thereof, it is portable. The bag compression means may be manual and be embodied by plates compressing the bag by means of translation or rotation of the plates, or translation of one of the plates towards the other which remains stationary, or be embodied by a compartment wherein the bag is housed.

In one particular embodiment of the pulsating medical assembly, the bag compression means are controlled electromechanically.

In one particular embodiment of the pulsating medical assembly, the pulsating device and the inflation means are integral.

One embodiment of the invention will now be described with reference to the appended figures, wherein:

FIG. 1 represents a longitudinal section of the pulsating device according to the invention when the balloon is deflated;

FIG. 2 represents a longitudinal section of the pulsating device according to the invention when the balloon is inflated.

Figure 3:
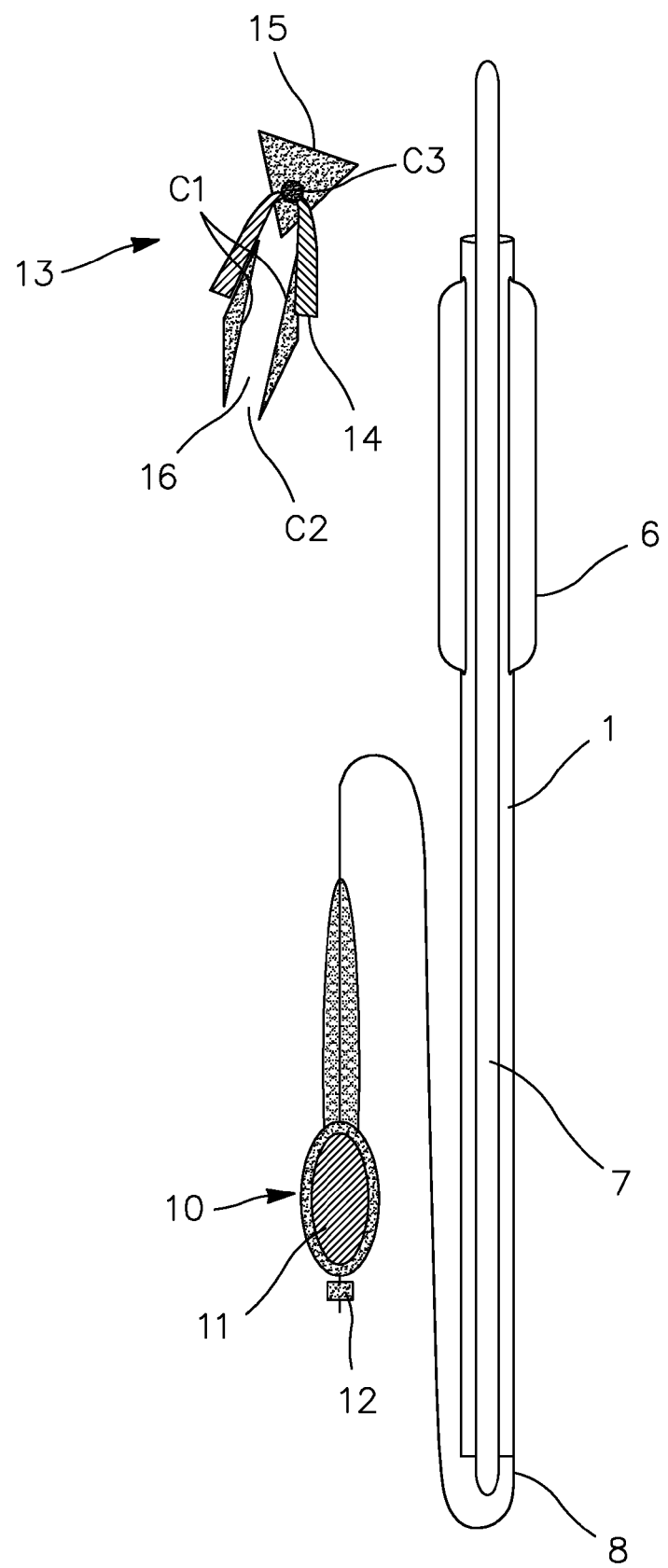
FIG. 3 represents a longitudinal section of the pulsating device according to the invention connected to one particular embodiment of the inflation means.

The pulsating device according to the invention, represented in FIGS. 1, 2 and 3, consists of a catheter 1, which is a hollow tube, having three successive parts A, B and C. Part A, also referred to as a rod, is the first to be inserted into the patient's blood vessel. Said catheter 1 has an external wall 2 and two ends 3 (part A side) and 4 (part C side). Part B of the catheter 1 has a recess 5 in the external wall 2. This recess 5 runs along the length B and is present on the entire circumference of the catheter 1. Due to the presence of this recess 5, parts A and C of the catheter 1 have substantially the same diameter, part B having a smaller diameter. An inflatable balloon 6 is positioned as in the prior art, i.e. for example, by bonding in the recess 5 of the catheter 1. The recess 5 is such that the diameter of part B of the catheter fitted with the deflated balloon is substantially equal to the diameters of parts A and C. Inside the catheter 1, a metal guide 7 is inserted. A fluid connection port 8, integrated in the wall of the catheter 1, adjoins the inflatable balloon 6 and inflation means 9 represented schematically, in FIGS. 1 and 2, at the end 4, said inflation means possibly being a console.

In FIG. 1, the balloon 6 is deflated; for this reason, the diameter of part B of the catheter 1 with the deflated balloon 6 is substantially equal to the diameter of parts A and C of the catheter 1.

In FIG. 2, the balloon 6 is inflated, the diameter of part B of the catheter 1 with the inflated balloon 6 is then greater than the diameter of parts A and C of the catheter 1.

The insertion of the pulsating device according to the invention will now be described. One of the patient's blood vessels is pricked with a needle, creating an opening, or insertion point. The metal guide 7 is then fitted. The catheter 1 is then inserted via said opening using the guide 7. Parts A, B and C of the catheter 1 pass through this opening in succession, not causing any widening of said opening since, as mentioned above, parts A and C and part B, fitted with the deflated balloon 6, have substantially the same diameter. Once the catheter 1 is in position, i.e. once the balloon 6 occupies the region of the blood vessel to be treated, the insertion point is then filled perfectly by part C of the catheter and the blood flow is thus reduced or stopped.

FIG. 3 represents the catheter 1 in FIG. 2 connected to one particular embodiment of the inflation means 9.

Said inflation means 9 comprises:
a first part including a bag 10 filled with fluid 11, connected at one end to the fluid connection port 8 and at the other end thereof to an anti-reflux valve 12, and
a second part including compression means 13 of said bag 10 comprising a bag compression compartment 14 and a control 15, by electromechanical means, for example, of said compression compartment 14. The bag compression compartment is represented schematically in a roughly rectangular shape with two long sides C1 and one of the short sides C2 open, whereas the second C3 is connected to the electromechanical control 15 represented schematically by a triangle. The compression compartment 14 thus has a recess 16.

The catheter 1 according to the invention is inserted into a patient's blood vessel, as described above. The end of the fluid connection port 8 projecting from the patient's body is connected to the bag 10. The bag 10 is then filled with fluid 11 (which may be helium, carbon dioxide, physiological saline solution) by opening the valve 12 (this operation may be performed prior to the connection of the fluid connection port 8 to the bag 10). The bag 10 is then inserted in the recess 16 of the compression compartment 14 controlled by the electromechanical control 15. According to the instructions received by said electromechanical control 15, a precise bag 10 compression/decompression rate is established, this rate possibly being, for example, 10 to 300 compressions per minute. The compression of the bag 10 gives rise to a flow of fluid 11 towards the balloon 6 which is inflated and the decompression of the bag 10 gives rise to an intake of fluid 11 from the balloon 6 to the bag 10, which deflates the balloon. A pulsating movement of the fluid is thus transferred from the bag 10 to the balloon 6. This catheter-balloon-inflation means assembly (as described in FIG. 3) thus forms a portable pulsating medical assembly. Indeed, the inflation means comprising the bag 10, the bag compression compartment 14 and the electromechanical control 15, is readily transportable by the patient when travelling, enabling the patient to retain some mobility.

The inflation means is low in cost and simple to use. Indeed, compression/decompression does not require a costly pressure source unlike the intra-aortic balloons according to the prior art.

Since the pulsating devices according to the invention can be applied to small-diameter catheters, small pulsating catheters will be available, which is currently not the case. These small pulsating catheters may be used in numerous applications.

Indeed, the inventor unexpectedly discovered that inflating the balloon, inserted into a blood vessel, increases the shear strength on the wall of the blood vessel.

These small pulsating catheters may thus be used not only for treating blocked coronary arteries (the smallest catheter diameter making it possible to reach the blocked region of the artery and the pulsating movement of the balloon enabling the gentle treatment of said region), but also for treating possible foetal malformations through umbilical vessels. Numerous other applications may be envisaged such as in angiogenesis-apoptosis interdependence (for example, increasing angiogenesis in the event of a fracture in an elderly subject in order to speed up healing), atherosclerosis (coronary, cerebral, renal), the immune system, cardiogenesis, nitrogen monoxide secretion (for example, for treating systemic or acute and above all chronic pulmonary arterial hypertension).

The invention claimed is:
1. A pulsating medical device, comprising:
a catheter, to be inserted into a blood vessel, comprising a tube having a diameter and including:
a first end;
a second end opposite said first end; and
a mid-section positioned between the first and second ends, the mid-section having a recess running along the length of the mid-section;
an inflatable component housed in the recess, the inflatable component being designed to be connected to an inflation means positioned at the second end, so that the inflatable component can be inflated or deflated in a pulsed manner,
characterised in that the diameter of the mid section of the catheter is less than the diameters of first end and the second end of the catheter and in that the diameters of the insertion end and the second end of the catheter are substantially equal.

2. The pulsating medical device according to claim 1, characterised in that the diameter of the mid section of the catheter plus the deflated inflatable component is less than or equal to the diameters of the first end and the second end of the catheter.

3. The pulsating medical device according to claim 1, characterised in that the inflatable component is a balloon.

4. The pulsating medical device according to claim 1, characterised in that the dimensions of the inflatable component are a length between 0.1 and 2 cm and a volume between 0.1 and 2 $cm^3$.

5. The pulsating medical device according to claim 1, characterised in that the inflatable component is formed from a biocompatible radio-opaque material.

6. The pulsating medical device according to claim 5, characterised in that the material is polyurethane.

7. The pulsating medical device according to claim 1, wherein the inflation means comprises:
   a bag suitable for being filled with fluid;
   a bag compression means suitable for compressing the bag in a pulsed manner; and
   a connection means connecting the bag to the inflatable component of the catheter, enabling the circulation of the fluid between the inflatable component and the bag.

8. The pulsating medical device according to claim 7, characterised in that the bag compression means are controlled electromechanically.

9. The pulsating medical device according to claim 7, characterised in that the pulsating device and the inflation means are integral.

10. A portable pulsating medical assembly, comprising:
    a catheter adapted to be inserted into a blood vessel, comprising a tube having a diameter and including:
       a first end having a rod adapted for insertion into the blood vessel;
       a second end opposite the first end and having a diameter substantially equal to a diameter of the first end; and
       a mid-section positioned between the first end and the second end, the mid-section including a recess along a length of the mid-section;
    an inflatable component adapted to be received by the recess between the first and second ends; and
    an inflation means adapted to be connected to the inflatable component for inflating or deflating the inflatable component in a pulsed manner, the inflation means comprising:
       a bag suitable for being filled with fluid;
       a bag compression means for compressing the bag in a pulsed manner; and
       a connection means for connecting the bag to the inflatable component, enabling the circulation of the fluid between the inflatable component and the bag.

11. A method of treating blocked coronary arteries, systemic or acute or chronic pulmonary arterial hypertension, comprising the steps of:
    providing a portable pulsating medical device, comprising:
       a catheter for insertion into a blood vessel, the catheter having an insertion end having a rod to be fitted into the blood vessel and an opposing second end; and a mid-section positioned between the insertion and second ends, the mid-section having a recess running along the length of the mid-section;
       an inflatable component housed around a mid section of the catheter and situated between the insertion end and second end;
       an inflation means for inflating or deflating the inflatable component in a pulsed manner; and
    fitting the rod into an opening of the blood vessel to allow the inflatable component to be inserted into the blood vessel;
    inserting the inflatable component into the blood vessel;
    connecting the inflation means to the inflatable component and filling the inflation means with a fluid; and
    compressing the inflation means in a pulsed manner.

12. The method according to claim 11, further including the step of using a needle to create an opening in the blood vessel.

13. The method according to claim 11, wherein the inflation means includes a bag for being filled with the fluid and for being compressed in a pulsed manner.

14. The method according to claim 13, wherein the bag is compressed in a pulsed manner by a compression compartment controlled by an electromechanical control to establish a precise bag compression/decompression rate.

* * * * *